United States Patent
Harris et al.

(10) Patent No.: US 6,750,312 B1
(45) Date of Patent: Jun. 15, 2004

(54) PROCESS FOR THE PREPARATION OF SUPPORTS FOR SOLID PHASE SYNTHESIS

(75) Inventors: Craig Stephen Harris, Macclesfield (GB); Donald Alfred Wellings, Northwich (GB); Francis Joseph Montgomery, Macclesfield (GB); Richard John Brown, Macclesfield (GB)

(73) Assignee: Avecia Limited, Manchester (GB)

( * ) Notice: Subject to any disclaimer, the term of this patent is extended or adjusted under 35 U.S.C. 154(b) by 0 days.

(21) Appl. No.: 09/980,587

(22) PCT Filed: May 25, 2000

(86) PCT No.: PCT/GB00/02007

§ 371 (c)(1),
(2), (4) Date: Mar. 26, 2002

(87) PCT Pub. No.: WO00/75171

PCT Pub. Date: Dec. 14, 2000

(30) Foreign Application Priority Data

Jun. 4, 1999 (GB) .................................. 9912911

(51) Int. Cl.$^7$ ..................... C08G 73/00; C08G 69/26; A61K 38/00; C07D 16/00; C07D 17/00

(52) U.S. Cl. ...................... 528/170; 528/310; 528/323; 528/328; 528/332; 528/342; 528/367; 528/368; 528/369; 528/480; 528/486; 530/333; 530/334; 530/335; 530/337; 530/338; 530/341; 562/442; 562/450; 525/54.1; 525/54.11

(58) Field of Search ................... 528/170, 310, 528/323, 328, 332, 342, 367, 368, 369, 480, 486, 312, 329.1; 530/333–335, 337–338, 341; 562/442, 450; 525/54.1, 54.11; 536/25.3

(56) References Cited

U.S. PATENT DOCUMENTS

| 5,049,651 A | * | 9/1991 | Heinz et al. | 528/480 |
| 5,635,598 A | * | 6/1997 | Lebl et al. | 530/334 |
| 5,882,645 A | * | 3/1999 | Toth et al. | 424/194.1 |
| 6,087,336 A | * | 7/2000 | Edwards et al. | 514/14 |
| 6,127,515 A | * | 10/2000 | Manfre et al. | 528/367 |
| 6,204,361 B1 | * | 3/2001 | Carpino et al. | 530/334 |
| 6,355,617 B1 | * | 3/2002 | Luke et al. | 514/16 |
| 6,376,649 B1 | * | 4/2002 | Semple et al. | 530/334 |
| 6,569,993 B1 | * | 5/2003 | Sledeski et al. | 530/333 |

FOREIGN PATENT DOCUMENTS

| EP | 0 360 062 | 3/1990 |
| EP | 0 884 327 | 12/1998 |
| WO | WO 94/02506 | 2/1994 |
| WO | WO 95/00165 | 1/1995 |
| WO | WO 95/00540 | 1/1995 |

OTHER PUBLICATIONS

Biopolymers Peptide Science, vol. 47, No. 5, 1998, Steven A. Kates et al, "High–Load" Polyethylene Glycol–Polystyrene (PEG–PS) Graft Supports for Solid–Phase Synthesis*, pp. 365–380.*

Biopolymers Peptide Science, vol. 47, No. 5, 1998, Neil J. Wells et al, "Solid–Phase Dendrimer Synthesis", pp. 381–396.*

* cited by examiner

Primary Examiner—P. Hampton Hightower
(74) Attorney, Agent, or Firm—Pillsbury Winthrop LLP

(57) ABSTRACT

A method for preparing a solid support material for carrying out a chemical reaction, said method comprising the following steps:

(i) reacting an amino functionalised solid material with a carboxylic acid having at least two similarly protected amino groups to form amide bonds between them, (ii) removing protecting groups in a single step, (iii) optionally repeating steps (i) and (ii) one or more times using the product of the preceding step as the amino functionalised solid material, and (iv) connecting a linkage agent to at least some of the free $NH_2$ groups of the product.

The method increases the loading capacity of the solid support material. It is particularly useful in connection with peptide synthesis.

25 Claims, No Drawings

PROCESS FOR THE PREPARATION OF SUPPORTS FOR SOLID PHASE SYNTHESIS

This application is the National Phase of International Application PCT/GB00/02007 filed May 25, 2000 which designated the U.S. and that International Application published under PCT Article 21(2) in English.

The present invention relates to a method of preparing support materials useful in solid phase chemical synthesis processes together with the solid materials produced thereby and intermediates used in the process. The support materials are useful in solid phase synthetic processes for the production of a variety of organic molecules, in particular peptides.

The multi-stage synthesis of an organic molecule typically involves numerous isolation steps to separate intermediates, produced at each stage, before progressing to the subsequent stage. These intermediates often require purification to remove excess reagents and reaction by-products and will include procedures such as precipitation, filtration, bi-phase solvent extraction, solid phase extraction, crystallisation and chromatography.

If the reaction chemistry is well defined, many of the isolation procedures used in solution phase synthesis are avoided by reversibly attaching the target molecule to a solid support in a way analogous to the use of a protecting group in a traditional synthesis. Excess reagents and some of the side-products can thereby be removed by filtration and washing of the solid support. Providing that the reactions are efficient and no solid support is lost, the target molecule is recovered in essentially quantitative yield, an objective rarely achieved in solution phase synthesis. In addition the time required to perform operations on a solid support is generally accepted to be a fifth of that required to carry out the equivalent stage in a solution phase synthesis. Another advantage of the solid phase approach is that the whole assembly is carried out in a single reactor.

There are disadvantages to the solid phase approach however. In particular, commercially available supports commonly used for solid phase synthesis of peptides allow a comparatively low loading (<1mmol/g) of reagent, resulting in reactions being carried out at a higher dilution than would normally be achievable in solution. To counteract this, reagents used to carry out the stepwise solid phase assembly are normally used in large excess (3–6 equiv.) and although the excesses are readily removed in the solid phase approach this can add an unnecessary burden on the economics of the process.

Some improvements in terms of increasing the loading of the solid support and solid phase peptide synthesis have been reported. Epton, R. et al; (1985); *Int. J. Biol. Macromol.*, 7, 287–298 describes the use of a bead-form phenolic core polymer as a support matrix. Modified forms of this matrix material, in which the phenolic core is condensed with protected tyrosine are described by Epton, R. et al., in *Peptides* 1986, *Proceedings of the 19th European Peptide Symposium*, Ed., Theodoropolulos, D.; Publ., Walter de Gruyter, Berlin, 1987, p151–154.

Kates et al., Peptide Science, 47, 5, 1998, 365–380 describes the introduction of polyethylene glycol into solid phase supports to increase the hydrophilicity of the support. Ornithine which is differently protected on each amino group was added to amino functionalised polystyrene, and one protecting group removed so as to allow for bond formation with polyethylene glycol (PEG) by way of a carboxylic acid group which is thereby introduced into the chain. This increases the number of available linking groups, but the loading of the resins was only 0.3–0.5 mmol/g. Solid phase dendrimer synthesis involving repeated treatments of a functionalised support with methyl acrylate and 1,3-propanediamine to produce a structure branched as a result of the production of tertiary amine groups has been described by Wells et al., Peptide Science, 47 (1998) 385–396.

The applicants have found a method by which a support can be modified using simple process steps to significantly increase the loading capacity, in particular for peptide synthesis, where it is particularly suitable and economic for large scale manufacture of peptides.

The present invention provides a method for preparing a solid support material for carrying out a chemical reaction, the said method comprising the following steps:

(i) reacting an amino functionalised solid material with a carboxylic acid having at least two similarly protected amino groups to form amide bonds between them, (ii) removing the protecting groups in a single step, (iii) optionally repeating steps (i) and (ii) one or more times, using the product of the preceding step as the amino functionalised solid material, and (iv) connecting a linkage agent to at least some of the free $NH_2$ groups of the product.

The product of this method is an amino functionalised branched amide-containing organic structure with the amino groups connected to a linkage agent.

This method provides a simple means of increasing the loading capacity of a support material without the need for complex chemical processing. The number of sites available to attach to linkage agents increases as a result of the production of branches. The number of branches available in step (iv) will depend upon the number of $NH_2$ groups present in the final product, and this is a function of the number of free $NH_2$ groups within the carboxylic acid structure and the number of times step (iii) is repeated.

The carboxylic acid used in the process is suitably an amino acid containing more than one amino group. Conveniently, this may comprise a naturally occurring amino acid such as lysine or ornithine but synthetic acids may also be used.

Suitable protecting groups for use in the process would be understood in the art, as would the means by which they may be added and subsequently removed. Examples of suitable protecting groups include 9-fluorenylmethoxycarbonyl (Fmoc) and tert-butoxycarbonyl (Boc). Protected forms of amino acids such as Fmoc and Boc protected forms are known in the art or they can be prepared using conventional methods.

The coupling reaction (i) and the reaction of step (iv) above are suitably carried out in an organic solvent such as N,N-dimethylformamide (DMF) or N-methylpyrrolidinone (NMP) in the presence of a coupling reagent. Coupling reagents include those known in the art of peptide synthesis, see for example those coupling reagents disclosed by Wellings, D. A.; Atherton, E.; in *Methods in Enzymology*, Publ., Academic Press, New York (1997) incorporated herein by reference, such as those comprising carbodiimides, especially dialkyl carbodiimides such as N,N'-diisopropylcarbodiimide (DIC), and reagents that form active esters, particularly benzotriazole active esters in situ, such as 2-(1H-benzotriazole-1-yl)-1,1,3,3-tetramethyluronium tetrafluoroborate (TBTU) or benzotriazole-1-yloxy-tris-(dimethylamino)phosphonium hexafluorophosphate (BOP), optionally in the presence of a base such as diisopropylethylamine (DIPEA) or N-methylmorpholine (NMM); or any other suitable activating agent common in the art of peptide synthesis.

The deprotection reaction conditions used in step (ii) will depend largely on the nature of the particular protecting group used and will be readily apparent to chemists. For instance, reaction with a base such as piperidine will result in the removal of protecting groups such as Fmoc groups and the reaction is suitably effected in an organic solvent such as N,N-dimethylformamide (DMF) or N-methylpyrrolidinone (NMP).

As used herein, the term "branched amide-containing organic structure" describes organic moieties which have a plurality of optionally substituted hydrocarbyl chains, each of which may be for example of from 2 to 12 suitably from 2 to 8 carbon atoms in length, and may be optionally interposed by a heteroatom, such as oxygen, nitrogen and sulphur. At least some of the chains are linked together by way of amide bonds, formed during the method of the reaction. Each chain of hydrocarbyl atoms may itself be branched. At least some, and preferably substantially all of the chains of the branched structure will carry a linkage agent or a protected form thereof.

Optional substituents on the hydrocarbyl chains may include any group which does not interfere with the subsequent reactions to which the support material will be subjected. Oxo substituents will be present as a matter of course on the hydrocarbyl chains as a result of the formation of amide bonds in the branched structure. Other possible substituents include substituted amines such as di-alkyl amines, further oxo substituents, ether groups such as alkyl ethers, thioethers such as alkyl thioethers, alkenyls, alkynyls, nitro, halo in particular fluoro and amides such as alkylamides.

Similarly, heteroatoms such as sulphur, oxygen and nitrogen, may be interposed in the hydrocarbyl chains, in addition to the nitrogen atoms present as a result of the formation of the amide bonds, provided they do not interfere with the subsequent reaction.

As used herein, the expression "hydrocarbyl" refers to any structure comprising carbon and hydrogen atoms. For example, these may comprise or be derived from alkyl, alkenyl, alkynyl, aryl, heterocyclyl, alkoxy, aralkyl, cycloalkyl, cycloalkenyl or cycloalkynyl groups. Groups derived from alkyl groups are for example alkylene groups, and from alkenyl groups are alkenylene groups, etc.

In this specification the term 'alkyl' when used either alone or as a suffix includes structures containing up to 20, preferably up to 10 and more preferably up to 6 carbon atoms. Similarly the terms "alkenyl" and "alkynyl" refer to unsaturated straight or branched structures containing for example from 2 to 20, preferably from 2 to 10 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

"Heteroaryl" refers to those groups described above which have an aromatic character. The term "aralkyl" refers to aryl substituted alkyl groups such as benzyl.

As used herein, the term "linkage agent" refers to a molecule which can link between the branched solid support material and an assembling molecule to allow it to take part in subsequent reaction procedures, and subsequently be cleaved to release the product undamaged from the support. Such molecules may bear protecting groups such as 9-fluorenylmethoxycarbonyl (Fmoc) and tert-butoxycarbonyl (Boc) which may be removed to allow the linkage agent to take part in a subsequent reaction. Examples of suitable linkage agents are those listed for example in Methods in Enzymology, Publ, Academic Press, New York, Section I, p126–174 (incorporated herein by reference). In particular they will comprise linkage agents used in peptide synthesis and which can couple to amino functionalised supports such as 4-[[1-(9-fluoren-9-yl)-methoxyformamido]-2,4-dimethoxybenzyl]-phenoxyacetic acid (the 'Rink' linkage agent, the group called herein "Fmoc-Linker-Am-OH", of structure (i)),

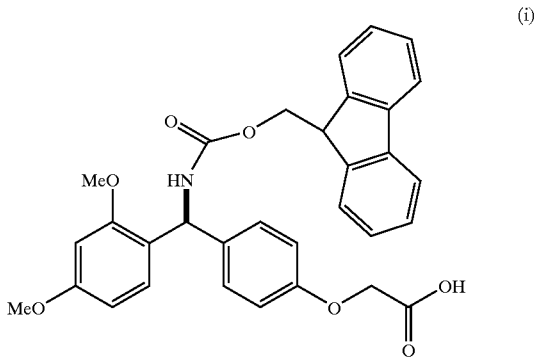

(i)

as well as 4-hydroxymethylbenzoic acid, 4-hydroxymethylphenoxy acid or any other linkage agents recognised in the art of solid phase synthesis.

The number of branches and therefore the potential number of linkage agents which may be conveniently and advantageously attached to the polymeric material will depend on steric factors, such as the length of the chains within the branched amide-containing structure, as well as to the nature of the linkage agent used and the purpose to which the material is to be put. However, in general, the process is effected such that the support material obtained has from 2–10 branches, such as from 2–8 branches, and preferably about 4–6 branches in each structure. These can be coupled to linkage agents or protected forms thereof, and so be available for synthesis reactions.

One embodiment of the method of the invention, where in step (iii), steps (i) and (ii) are repeated once to yield four free amino groups, is represented schematically in Scheme 1 hereinafter. In this scheme, following representations apply:

S is a solid polymer core, with a single reactive site illustrated;

$R^1$ is an organic moiety with n+1 available points for bonding:

$R^2$ is an organic moiety with m+1 available points for bonding;

$R^3$ is either a bond or an organic bridging group;

$R^4$ and $R^5$ are protecting groups;

L is a linkage agent, or a protected form thereof;

p is an integer of 1 or more, for example from 1 to 6, provided that p is 1 when $R^3$ is a bond; and n and m are independently selected from integers of 2 or more, for example from 2 to 8 and preferably from 2 to 4 and most preferably 2 or 3.

Suitable compounds of formula (I) are well known in the art. The solid polymer core 'S' in formula (I) may comprise polymers such as polyacrylamides, polystyrene or co-polymeric materials as well as inorganic solids such a glass or silica. Some of these reagents have amino functional groups available on the surface. In this case, in compounds of formula (I), $R^3$ may be a bond, although a spacer group may be added if required. In other cases, the solid material as supplied may comprise different functional groups at the surface and in those cases, amino substituents must be introduced in a preliminary step. Methods by which this can be achieved are well known in the art. For example, polymeric materials with acid or ester functionalities at the surface may be reacted with primary or secondary amines as appropriate to form an amide bond and therefore complete the bridging group $R^3$. In particular, reaction with an amine of formula (X)

$$H_2N—[(R^8)_zNH)]_y(R^{8'})_x—NH_2 \quad\quad (X)$$

where x is an integer of 2 or more, suitably from 2 to 6, y is 0 or an integer of 1 or more, suitably from 1 to 5, and each group z is independently 2 or more, for example from 2 to 6, and each $R^8$ and $R^{8'}$ are the same or different and are optionally substituted divalent hydrocarbyl groups, in particular optionally substituted alkylene groups and especially (—CH$_2$—), In these compounds, y+1 will be equal to p.

A particular example of a compound of formula (X) are diamines such as those of general formula (XI)

$$NH_2—(CH_2)_x—NH_2 \quad\quad (XI)$$

where x is as defined above. A particular example of such an amine is ethylene-diamine.

Where p is greater than 1, the group $R^3$ will bear more than one amino group and so the number of branches formed during the subsequent reaction stages will increase. Suitably therefore, in the compound of formula (X), y is 1 or more. An example of a multiple amine of formula (X) is diethylenetriamine (i.e. H$_2$N—(CH$_2$)$_2$—NH—(CH$_2$)$_2$—NH$_2$).

Suitable bridging groups $R^3$ include optionally substituted hydrocarbyl chains of at least two carbon atoms and for example from 2–12 carbon atoms which may itself be interposed with a heteroatom such as oxygen, nitrogen and sulphur. Examples of such groups include, for example, groups of formula —(CR$^9$R$^{10}$)$_a$—, —R$^{11}$—(CR$^9$R$^{10}$)$_a$R$^{11}$ (CR$^9$R$^{10}$)$_b$—, where each $R^9$ and $R^{10}$ is independently selected from hydrogen or an optional substituent as described above, and $R^{11}$ is a cycloalkylene or arylene group, and a and b are independently selected from 2 to 12.

Thus the nature of bridging groups $R^3$ in the compounds of formula (I) to (IX) will depend to some extent upon the particular core polymer S used and the groups required to link to functionalities on the surface. In general, the bridging group will comprise a hydrocarbyl chain linked to the support S and one or more functional group derivatives such as amino, mono- or di-alkylamino or hydroxy groups. Thus an example of a bridging group $R^3$ is a group of sub formula (XII)

$$—R^{12}(NH)_p— \quad\quad (XII)$$

where $R^{12}$ is $C_{2-6}$ alkylene optionally interposed with for example oxygen, phenylene; $C_{3-8}$ cycloalkylene or —(CH$_2$)$_r$R$^{13}$— where $R^{13}$ is phenylene or $C_{3-8}$ cycloalkylene, and where p is as defined above.

Particular examples of bridging groups $R^3$ are

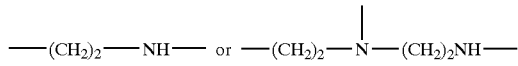

A particularly preferred compound of formula (I) is derived from a commercially available (Polymer Laboratories) solid, sold, under the catalogue name PL-DMA. PL-DMA is prepared by copolymerisation of acryloyl-sarcosine methyl ester, N,N-dimethylacrylamide and bis-acryloylethylenediamine. The procedure for preparation of the polymer core has been described by Atherton, E.; Sheppard, R. C.; *In Solid Phase Synthesis: A Practical Approach*, Publ., IRL Press at Oxford University Press (1984) (incorporated herein by reference). In the commercially available form, the functional loading of the starting polyacrylamide supplied is 1 mmol/g. The functional group on the PL-DMA is a methyl ester and this is initially converted to a primary amine functionality by reaction with an alkyl amine as described above.

Thus suitable solid supports of formula (I) include those listed in Table 1.

TABLE 1

| Name | Structure | Comments |
| --- | --- | --- |
| Aminomethylpolystyrene | 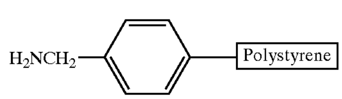 | Available from most catalogue suppliers (e.g.'s. Bachem, Novabiochem, Advanced Chemtech). |
| Aminopolyethyleneglycolpolystyrene |  | Amino functionalised polyethyleneglycol (PEG) on a polystyrene core is commercially available under the trade name Tentagel. A similar support is available from Perkin-Elmer. |
| Amino PEG (PEGA) resin | PEGA resins are a copolymer of dimethyl acrylamide, mono-2-acrylamidoprop-1-yl[2-aminoprop-1-yl]polyethylene glycol and bis-2-acrylamidoprop-1-yl polyethylene glycol. | Commercially available from Novabiochem and Polymer Laboratories. |
| Pepsyn/Polyhipe resins | N,N-dimethylacrylamide (DMA) supported within a rigid macroporous structure. | Commercially available from Novabiochem |
| Inorganic supports | Amino functionalised | e.g.'s controlled pore glass, silica. |

Suitable organic moieties for $R^1$ and $R^2$ in compounds of formulae (II) and (V) respectively include optionally substituted hydrocarbyl groups which may be optionally interposed with heteroatoms such as oxygen, sulphur and nitrogen, or with carbocyclic or heterocyclic rings. The precise nature of these groups is not critical provided that they are inert in the subsequent application to which the support material can will be placed. Preferably however, the compounds of formula (11) and (V) are protected forms of lysine or ornithine (where n and m are 2), and are preferably protected lysine. Suitable protecting groups $R^4$ and $R^5$ are described above and include Fmoc and Boc, but preferably Fmoc.

Thus where the compound of formula (II) is lysine, the completion of Scheme 1 will result in the production of a compound of formula (IXA)

(IXA)

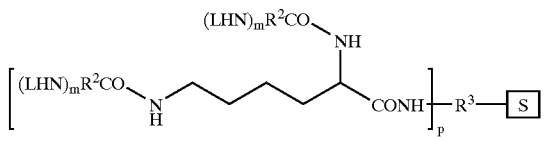

where S, $R^3$, $R^2$, L, m and p are as defined above. Where the compound of formula (V) is also protected lysine, m is 2. It can be seen therefore, that where amino acids having two amino groups such as lysine or ornithine are used in the process of the invention, the total number of linkage agents L attached to each available site on the support molecule has been quadrupled following only one operation of step (iii) above. The level of branching can therefore be varied depending upon the number and nature of the amino acid residues interposed between the solid support and the linking groups.

Solid support materials obtainable by the process of the invention are novel and these form a further aspect of the invention. In particular there is provided a compound of formula (IX) as illustrated in Scheme 1, wherein $R^1$, $R^2$, $R^3$, L, n, m and p are as defined above.

The precursors of these compounds (i.e. compounds VI and VII of Scheme 1 wherein $R^1$, $R^2$, $R^3$, n, m and p are as defined above) are also novel and form further aspects of the invention. Thus the invention further provides a compound of formula

XIII

wherein S, $R^1$, $R^2$, $R^3$, n, m and p are as defined in above, and $R^{20}$ is hydrogen or an amino protecting group.

In these compounds, preferred values for the variables $R^1$, $R^2$, $R^3$, n, m and p, are as described above.

The solid support materials are suitable for use in the solid phase synthesis of a range of compounds including peptides. Thus in a further aspect, the invention provides a method for preparing a compound, which method comprises binding a reagent to a linkage agent of the support material of the invention, effecting one or more reaction steps to generate product, and thereafter cleaving said product from the support material.

Using a solid support material in accordance with the invention, any required peptide can be prepared, for example using chemistry and techniques employed in traditional Fmoc-based solid phase peptide synthesis (Wellings, D. A.; Atherton, E.; In *Methods in Enzymology*, Publ., Academic Press, New York (1997) (incorporated herein by reference). The peptide can then be cleaved from the support and worked up using standard conditions (Wellings D. A. supra-incorporated herein by reference). Examples of peptides which can be prepared in this way include the peptides described in WO 97/31023 and other therapeutic peptides.

In general peptides will be produced in a stepwise manner as illustrated hereinafter. Specifically, peptides are prepared by coupling a protected amino acid to a linkage agent immobilised on a solid support, deprotecting the amino acid and thereafter coupling a further protected amino acid to said first amino acid and repeating said process until the desired peptide is produced. At the end of the sequence, the peptide is cleaved from the solid support. Suitably the coupling reaction is effected in a solvent such as N,N'-dimethylformamide (DMF) with an activated species prepared using a coupling reagent such as N,N'-diisopropylcarbodiimide in the presence of a compound that forms an active ester with such a coupling agent such as 1-hydroxybenzotriazole (HOBt). Cleavage is suitably effected by addition of piperidine, although this will depend to some extent on the nature of the linkage agent as would be understood in the art.

The applicants have found that where the amino acid is a protected 4-aminophenyl acetic acid (PAPA), a preferred coupling agent is 2-(1H-benzotriazole-1-yl)-1,1,3,3-tetramethyluronium tetrafluoroborate (TBTU). Furthermore, a preferred base is diisopropylethylamine (DIPEA). Such reactions, in particular when effected using the support materials described above, form a further aspect of the invention. In this further aspect of the present invention, it is preferred that in couplings where the amino acid is other than a protected 4-aminophenyl acetic acid (PAPA), a preferred method is to use an activated species prepared using a coupling reagent such as a carbodiimide, often a dialkyl carbodiimide, and preferably N,N'-diisopropylcarbodiimide, in the presence of a compound that forms an active ester, such as 1-hydroxybenzotriazole (HOBt).

The invention will now be particularly described by way of example, with reference to the accompanying diagrammatic schemes in which Scheme 1 is a generalised scheme illustrating the method of the invention, and Scheme 2 is a reaction scheme illustrating the preparation of a material of the invention and its use in the production of a target peptide.

EXAMPLE 1

Preparation of Solid Reaction Support

Step 1

Reaction of Ethylene-diamine with PL-DMA

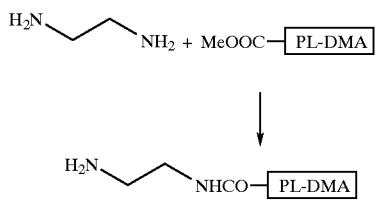

PL-DMA resin (5.00 g, 5.00 mmol) available from Polymer Laboratories with a molecular weight of 1000, was charged to a 500ml flask equipped with overhead stirrer. Ethylene-diamine (150 ml) was added and stirred for 18 hours. The resin derivative was filtered through 500 ml sintered glass funnel fitted with a 1 L Buchner flask and equipped with overhead stirrer. The filter cake was slurry washed with portions of DMF (60 ml) until the pH of the filtrate was <8 as indicated by moistened pH paper.

Step 2

Fmoc-Lys(Fmoc)OH Coupling

N-Hydroxybenzotriazole (HOBt) (2.27 g, 16.7 mmol, 3.33 equiv.) was charged to a clean dry 250 ml flask equipped with a magnetic stirrer. A protected lysine derivative Fmoc-Lys(Fmoc)-OH (7.38 g, 12.5 mmol, 2.50 equiv.), was added. This compound, of formula,

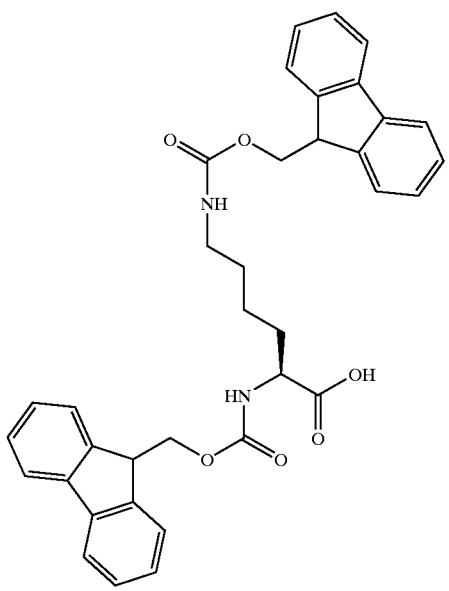

is commercially available from suppliers of reagents and materials for peptide synthesis.

The contents were then dissolved in DMF (50 ml) and the solution chilled to between 0–5° C. Diisopropylcarbodiimide (DIC) (1.75 g, 2.18 ml, 13.8 mmol, 2.75 equiv.) was added whilst keeping the solution below 5° C. The mixture was stirred for 10 minutes at 0–50° C.

A slight nitrogen/argon pressure was applied to the resin product of Step 1, and the mixture added to it with a DMF (5 ml) rinse and stir. After 5 minutes, extra DMF (50 ml) was added to allow mobilisation of the resin. The mixture was then left for 1 hour. Completion of the reaction was checked by removing approximately 5 mg of beads from the resin bed and carrying out a Kaiser test. In this test, ninhydrin (5% w/v in n-butanol, 6 drops) and phenol (80% w/v in n-butanol, 6 drops) are added to the test tube containing the beads to be tested and heated to 100° C. for 5 minutes. A positive result was indicated by a blue colouration of the beads and/or the solution is observed. A negative result was indicated when the blue colour of the beads and solution is not seen. The product was filtered under vacuum and slurry washed with DMF (10×50 ml).

The Fmoc protecting groups were then removed by addition of piperidine (20% v/v in DMF, 80 ml) followed by a vacuum filtration step, a procedure which was effected twice (3 and 7 minute treatments). The product was then washed with DMF (5×80 ml). After each wash, a vacuum filtration step was effected. HOBt (10% w/v in DMF, 80 ml) was added with stirring. After 5 minutes, further DMF was added as required to mobilise the resin which was stirred for a further 15 minutes and then filtered under vacuum.

A solution of HOBt (10% w/v in DMF, 80 ml) was stirred for 5 minutes after which sufficient extra DMF was added so as to mobilise the resin, which was then stirred for a further 15 minutes. The product was filtered under vacuum and slurry washed with DMF (5×80 ml) until the filtrate had a pH<8 as indicated by moistened pH paper.

Step 3

Further Fmoc-Lys(Fmoc)-OH Coupling

To a clean dry 250 ml flask equipped with a magnetic stirrer was added HOBt (4.55 g, 33.3 mmol, 6.67 equiv.) and Fmoc-Lys(Fmoc)-OH (14.8 g, 25 mmol, 5.0 equiv.) which were dissolved in DMF (75 ml). The solution was cooled to 0–5° C. and DIC (3.51 g, 4.35 ml, 27.5 mmol, 5.5 equiv.) added whilst keeping the solution below 5° C. and stirring for 10 minutes.

A slight nitrogen/argon pressure was applied to the resin from Step 3 and the resultant cooled solution added to the resin with a DMF (5 ml) rinse and stirring. After 5 minutes, extra DMF (50 ml) was added and the mixture left for 1 hour. Completion of the reaction was checked by removing approximately 5 mg of beads from the resin bed and carrying out a Kaiser test. The product was filtered under vacuum and slurry washed with DMF (10×80 ml), deprotected using piperidine (20% v/v in DMF) and HOBt added as described in Step 2. The reaction here can be illustrated by the following scheme:

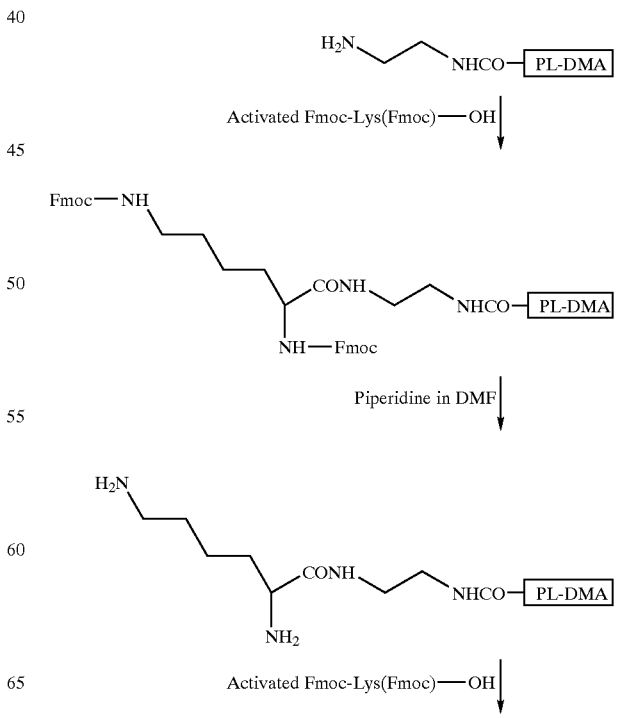

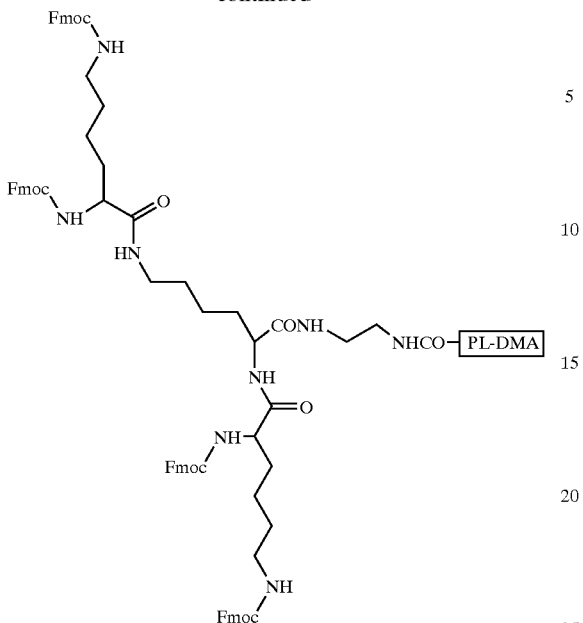

The final deprotected branched lysine construct can be written in the simplified form as follows.

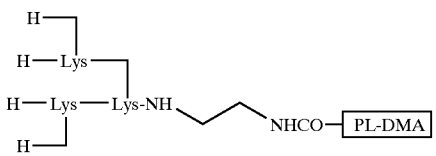

Step 4
Fmoc-LinkerAm-OH Coupling

HOBt (9.10 g, 66.7 mmol, 13.3 equiv.) and Fmoc-LinkerAm-OH (27.0 g, 50.0 mmol, 10.0 equiv.) were added to a clean dry 250 ml flask equipped with a magnetic stirrer and dissolved in DMF (60 ml). The Fmoc-LinkerAm-OH was of structure

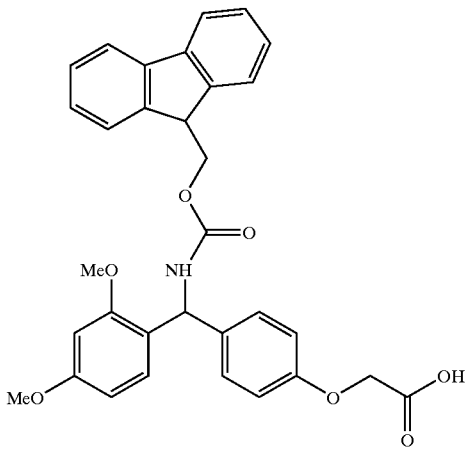

The solution was chilled to 0–5° C. and DIC (7.01 g, 8.70 ml, 55.0 mmol, 11 equiv.) added whilst keeping the solution below 5° C. The mixture was stirred for 10 minutes at 0–5° C., after which it was added to the resin of Step 3 to which a slight nitrogen/argon pressure was added.

This step is illustrated by the following scheme:

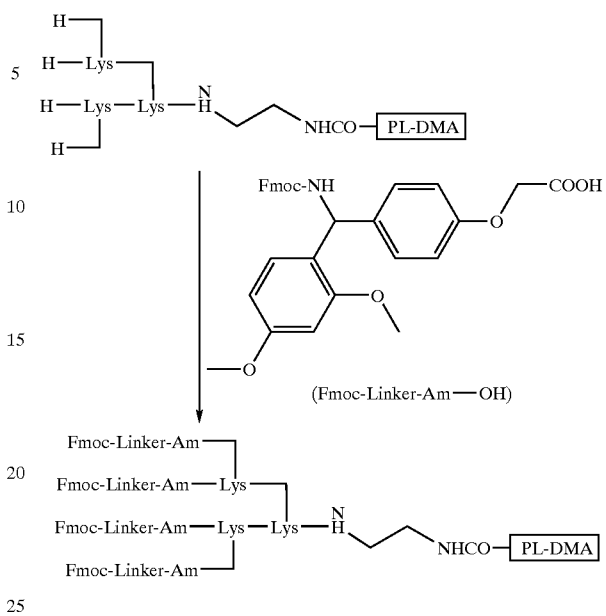

The completion of the reaction was checked by removing approximately 5 mg of beads from the resin bed and carrying out a Kaiser test. The product was then washed and deprotected as described in Step 2. This functionalised resin was then ready for peptide synthesis.

EXAMPLE 2

Step 1
Peptide Fmoc-Papa-OH Coupling 2-(1H-Benzotriazole-1-yl)-1,1,3,3-tetramethyluronium tetrafluoroborate (TBTU) (15.4 g, 47.5 mmol, 9.50 equiv.) was added to a clean dry 250 ml flask equipped with a magnetic stirrer. To this was added a protected amino acid Fmoc-Papa-OH of structure

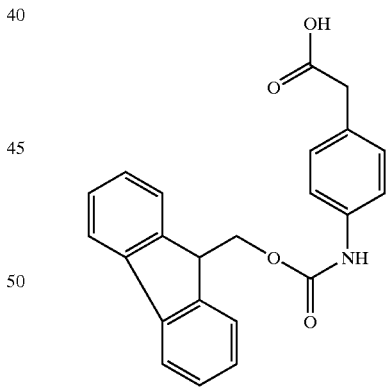

(18.9 g, 50.0 mmol, 10.0 equiv.) and the reagents dissolved in DMF (70 ml). After chilling the solution to 0–5° C., diisopropylethylamine (DIPEA) was added (7.75 g, 10.4 ml, 60.0 mmol, 12 equiv.) whilst keeping the solution below 5° C. The mixture was stirred for 10 minutes at 0–5° C. and then added to the resin from Example 1 under a slight nitrogen/argon pressure, together with a DMF (5 ml) rinse and stirring. The completion of the reaction was checked by removing approximately 5 mg of beads from the resin bed and carrying out a Kaiser test. The product was then washed and deprotected as described in Example 1 Step 2 above. Fmoc-Papa-OH was obtained as follows:

Fmoc-Papa-OH

To a slurry of 4-aminophenylacetic acid (Papa) (30.0 g, 19.5 mmole, 1.0 equiv.) in acetone (600 ml) and aqueous sodium bicarbonate (36.13 g, 428 mmole, 2.2 equiv. in 600 ml water) was added 9-fluorenylmethyl-succinimidyl carbonate (Fmoc-OSu) (70.3 g, 204 mmole, 1.05 equiv.) with stirring. After stirring overnight at room temperature the resulting slurry was acidified with concentrated hydrochloric acid (42.3 ml, 486 mmole, 2.5 equiv.) and the product extracted at 45° C. into n-butyl acetate (2×600 ml) when the organic extract was washed twice at 45° C. with water (2×300 ml), distilled under vacuum on a steam bath to 450 ml and crystallised over 2 hours to room temperature. The crystalline product was isolated and washed twice with n-butyl acetate (2×120 ml) and dried at 60° C. in a vacuum oven. Yield 67.2 g (92%)

Step 2

Fmoc-Ala-OH Coupling

In the next stage, HOBt (9.10 g, 66.7 mmol, 13.3 equiv.) and Fmoc protected alanine (Fmoc-Ala-OH) of formula

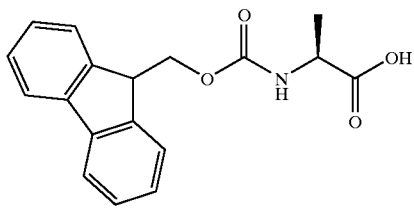

(16.6 g, 50.0 mmol, 10.0 equiv.) was added to a clean dry 250 ml flask equipped with a magnetic stirrer. The reagents were then dissolved in DMF (60 ml) and chilled as before to 0–5° C. DIC (7.01 g, 8.70 ml, 55.0 mmol, 11 equiv.) was added with stirring (10 minutes) whilst keeping the solution below 5° C.

The solution was then added to the product of Step 1 under a slight nitrogen/argon pressure, and rinsed and stirred in the presence of DMF as described in Step 1. The completion of the reaction was checked by removing approximately 5 mg of beads from the resin bed and carrying out a Kaiser test. The product was washed with DMF (5×100 ml). Acetic anhydride (10% v/v in DMF, 100 ml) was added and the mixture stirred for 1 hour. This capped any residual aniline groups. There followed further washing with DMF, deprotection with piperidine in DMF and further DMF washing as described above.

Step 3

Fmoc-Arg(Pbf)-OH Coupling

In this coupling, HOBt (9.10 g, 66.7 mmol, 13.3 equiv.) was used together with Fmoc-Arg(Pbf)-OH (33.9 g, 50.0 mmol, 10.0 equiv.) of formula

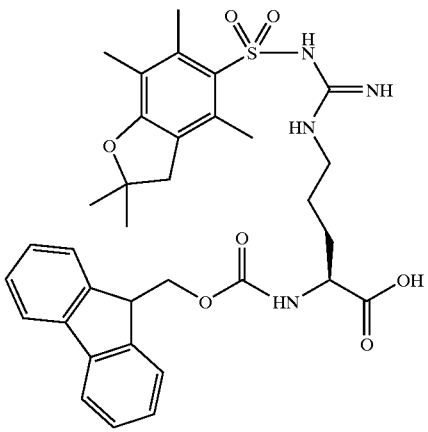

dissolved in DMF (80 ml) as the starting material. The solution was cooled to between 0–5° C. and DIC (7.01 g, 8.70 ml, 55.0 mmol, 11 equiv.) added whilst keeping the solution below 5° C. with stirring for 5 minutes. The product was added to the resin of Step 2 under a slight pressure of nitrogen/argon with a DMF (5 ml) rinse and stir.

After 5 minutes extra DMF (30 ml) was charged as required to mobilise the resin and this mixture was left for 1 hour. The completion of the reaction was checked by removing approximately 5 mg of beads from the resin bed and carrying out a Kaiser test. Washing with DMF and deprotection with piperidine in DMF was effected as described above in Example 1 Step 2.

Step 4

Fmoc-Ala-OH Coupling

Step 2 was repeated in order to link a further alanine residue to the developing peptide.

Step 5

Fmoc-Lactam Coupling

A further coupling reagent sample was prepared by dissolving HOBt (9.10 g, 66.7 mmol, 13.3 equiv.) and (2S)-2-[(3R)-3-(N-[9-fluorenylmethyloxycarbonyl]amino-2-oxopyrrolidin-1-yl]propionic acid (19.9 g, 50.0 mmol, 10.0 equiv.) of formula

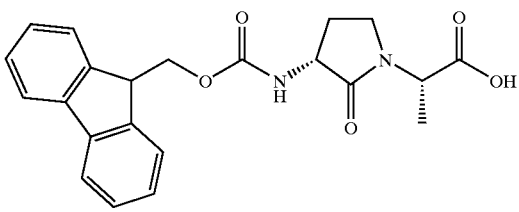

obtained as described in WO 97/31023, in DMF (70 ml) in a clean dry 250 ml flask equipped with a magnetic stirrer. After chilling to 0–5° C., DIC (7.01 g, 8.70 ml, 55.0 mmol, 11 equiv.) was added with stirring for 10 minutes whilst keeping the solution below 5° C.

The solution was then charged to the product of Step 4 under a small pressure of argon/nitrogen with a DMF (5 ml) rinse and stir. After 5 minutes, extra DMF (30 ml) was added to mobilise the resin which was then left for 1 hour. The completion of the reaction was checked by removing approximately 5 mg of beads from the resin bed and carrying out a Kaiser test.

Solvent was then removed under reduced pressure and the product treated with DMF and piperidine in DMF as described in Example 1 Step 2. The resin was then filtered under vacuum.

Step 6
 Fmoc-Ala-OH Coupling
 A further Fmoc protected alanine residue was coupled next by repeating the process of Step 2 above.
Step 7
 Fmoc-Arg(Pbf)-OH Coupling
 Step 3 was repeated.
Step 8
 Fmoc-Ala-OH Coupling
 The coupling of Step 2 was repeated.
Step 9
 Phv-OH Coupling
 In this coupling, the initial solution comprised HOBt (9.10 g, 66.7 mmol, 13.3 equiv.) and 5-phenylvaleric acid (Phv-OH) (9.00 g, 50.0 mmol, 10.0 equiv.) dissolved in DMF (70 ml).
 After chilling the solution to 0–5° C., DIC (7.01 g, 8.70 ml, 55.0 mmol, 11 equiv.) was added with stirring for 10 minutes whilst keeping the solution below –5° C. The solution was applied to the resin of Step 8 which had been kept under the slight nitrogen/argon pressure, together with a rinse solvent comprising DMF (5 ml) with stirring. After 5 minutes, extra DMF (80 ml) was added to mobilise the resin which was then left for 1 hour. A Kaiser test as described above was effected to check completion of the reaction and the solvent was removed under reduced pressure.
 After slurry washing the product, first with DMF (10×175 ml) and then with diethyl ether (5×175 ml), it was dried using a nitrogen purge on a sintered funnel for 10 minutes. Further drying was carried out at 40° C. in a vacuum oven overnight to constant weight.

EXAMPLE 4

Cleavage and Analysis of Product

The resin product from Example 3 (6.6 g) was transferred to a 250 ml flask and triethylsilane in trifluoroacetic acid (TFA) (10% v/v, 132 ml) added rapidly in one portion. The mixture was stirred for 2 hours, then filtered and the residue washed with triethylsilane in TFA (10% v/v, 2×50 ml). After evaporation of the filtrate to dryness on a rotary evaporator at 40° C., diethyl ether (100 ml) was added and the mixture stirred vigorously for 14 hours to precipitate the peptide. The precipitate was filtered on a sintered funnel, washed with diethyl ether (3×30 ml) and air dry on the sinter for 5 minutes. Further drying was carried out overnight at 40° C. in a vacuum oven. The target peptide (Scheme 1) was obtained.

In an alternative cleavage process, the resin product from Example 3 (20.0 g, 2.271 mmol) was added to a reactor and a slight nitrogen pressure applied. Triethylsilane (40.0 ml) and di-n-butyl ether (40.0 ml) were added and the contents were agitated at 0° C. Cooling was maintained in order to control the exotherm of the reaction and to limit impurity formation. TFA (300 ml) was added over a period of 1 hour and the mixture then agitated for 16 hours at 0° C.

The resultant suspension was then filtered under vacuum, washed twice with TFA (100 ml), and the wash materials and the filtrate combined. TFA was then distilled off under reduced pressure at 25° C. until only a trickle distilled.

The concentrate obtained was added to rapidly agitated diiso-propyl ether (400 ml) and the mixture stirred for 30 minutes at ambient temperature. The precipitate was collected by filtration, washed with diiso-propyl ether (100 ml) and the cake deliquored. The wash and deliquor step was repeated once and the product dried at 40° C. in a vacuum oven for 2 hours.

9.97 g of peptide was obtained.

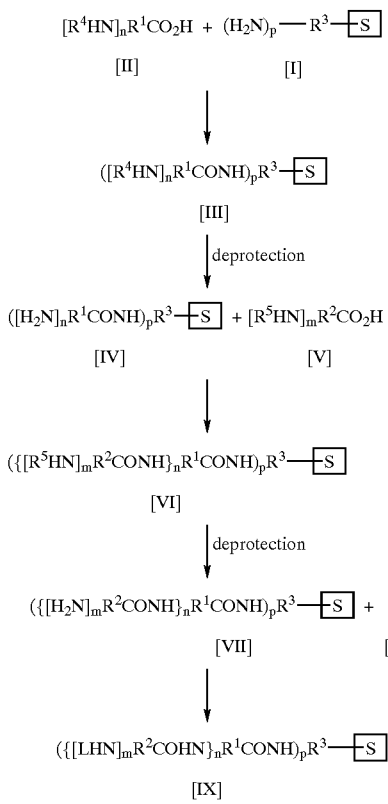

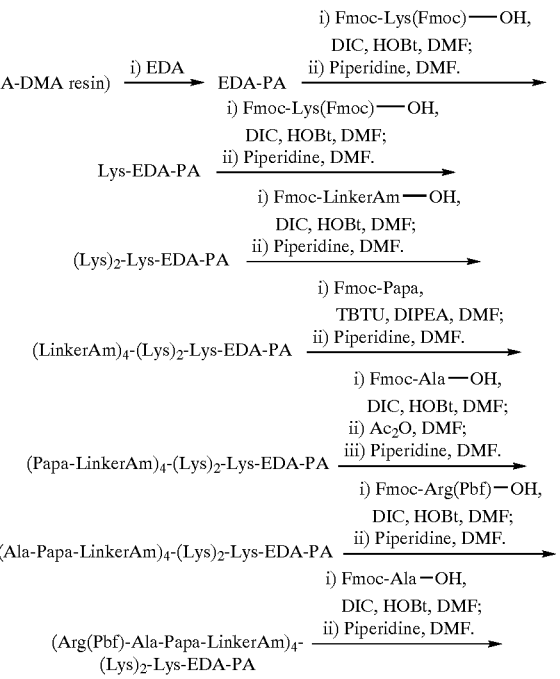

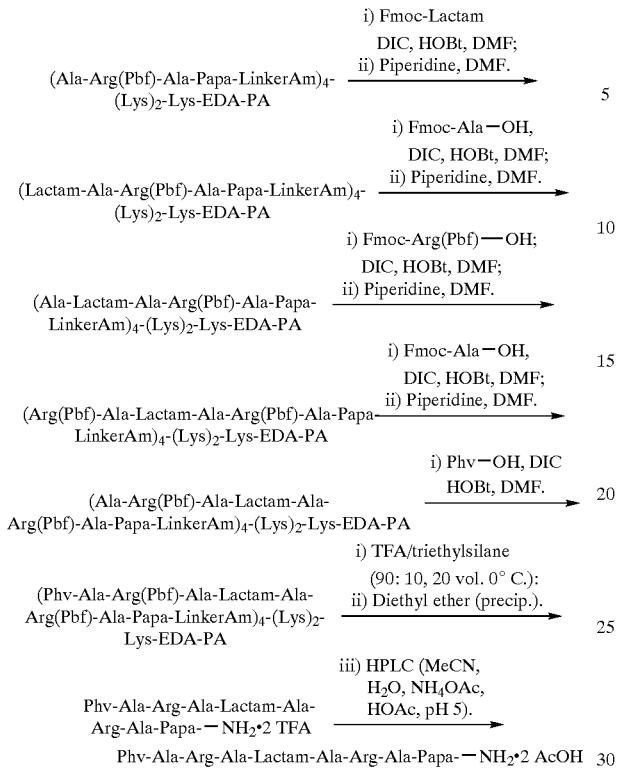

PA = Polyamide sarcosine resin, solid support
EDA = Ethylenediamine
Lys = Lysine (used twice to increase resin capacity × 4)
LinkerAm = Acid labile linkage agent
Phv—OH = 5-Phenylvaleric acid

What is claimed is:

1. A method for preparing a solid support material for carrying out a chemical reaction, said method comprising the following steps:
   (i) reacting an amino functionalised solid material with a carboxylic acid having at least two similarly protected amino groups to form amide bonds between them,
   (ii) removing protecting groups in a single step,
   (iii) optionally repeating steps (i) and (ii) one or more times using the product of the preceding step as the amino functionalised solid material, and
   (iv) connecting a linkage agent to at least some of the free $NH_2$ groups of the product.

2. A method according to claim 1 wherein the said carboxylic acid comprises an amino acid.

3. A method according to claim 2 wherein the amino acid is lysine or ornithine.

4. A method according to claim 1 or claim 2 wherein the amino functionalised solid material is obtained by reacting an acid or ester substituted support with a compound of formula (X)

where x is an integer of 2 or more, y is 0 or an integer of 1 or more, and each group z is independently 2 or more, and each $R^8$ and $R^{8'}$ are the same or different and are optionally substituted divalent hydrocarbyl groups.

5. A method according to claim 4 wherein the compound of formula (X) is ethylenediamine.

6. A solid support material obtainable by the method of claim 1.

7. A solid support material comprising a compound of formula (IX)

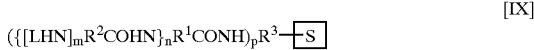

wherein S is a solid polymer core;
$R^1$ is a organic moiety with n+1 available points for bonding:
$R^2$ is an organic moiety with m+1 available points for bonding;
$R^3$ is either a bond or an organic bridging group;
L is a linkage agent, or a protected form thereof;
P is an integer of 1 or more, provided that p is 1 when $R^3$ is a bond; and
n and m are independently selected from integers of 2 or more.

8. A compound of formula (XIII)

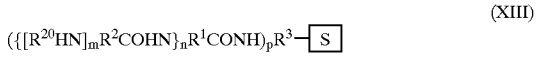

wherein
S is a solid polymer core;
$R^1$ is a organic moiety with n+1 available points for bonding;
$R^2$ is an organic moiety with m+1 available points for bonding;
p is an integer of 1 or more, provided that p is 1 when $R^3$ is a bond; and
n and m are independently selected from integers of 2 or more,
$R^3$ is either a bond or an organic bridging group formed by reaction of acid or ester functionalities at the surface of S with an amine of formula (X)

where x is an integer of 2 or more, y is 0 or an integer of 1 or more, each group z is independently 2 or more, and each $R^8$ and $R^{8'}$ are the same or different and are optionally substituted divalent hydrocarbyl groups and $R^{20}$ is hydrogen or an amino protecting group.

9. A method for preparing a compound, which method comprises binding a reagent to a linkage agent of a support material according to claim 6 or claim 7, effecting one or more reaction steps to generate product, and thereafter cleaving said product from the support material.

10. A method according to claim 9 wherein the product is a therapeutic peptide.

11. A method according to claim 10, wherein the therapeutic peptide is
Phv-Ala-Arg-Ala-Lactam-Ala-Arg-Ala-Papa-$NH_2$
or a pharmaceutically acceptable salt thereof, wherein Phv is a residue derived from 5-phenylvaleric acid and Papa is a residue derived from 4-aminophenyl acetic acid.

12. A method for preparing a peptide which comprises coupling a protected amino acid to a linkage agent immobilised on a solid support, deprotecting the amino acid and thereafter coupling a further protected amino acid to said first amino acid and repeating said process until the desired peptide is produced, and thereafter cleaving the peptide from the solid support, wherein the amino acid is a protected 4-aminophenyl acetic acid (PAPA), the coupling agent is 2-(1H-benzotriazole-1-yl)-1,1,3,3-tetramethyluronium tetrafluoroborate (TBTU) and the coupling is effected in the presence of diisopropylethylamine (DIPEA).

13. A method according to claim 12, wherein for couplings where the amino acid is other than a protected 4-aminophenyl acetic acid (PAPA) a coupling reagent comprising a carbodiimide is employed in the presence of a compound that forms an active ester.

14. A method according to claim 12 or 13, wherein the solid support comprises a solid support material for carrying out a chemical reaction, and prepared by a method comprising the following steps:

(i) reacting an amino functionalised solid material with a carboxylic acid having at least two similarly protected amino groups to form amide bonds between them, (ii) removing protecting groups in a single step, (iii) optionally repeating steps (i) and (ii) one or more times using the product of the preceding step as the amino functionalised solid material, and (iv) connecting a linkage agent to at least some of the free $NH_2$ groups of the product.

15. A method according to claim 14, wherein the carboxylic acid in step (i) comprises an amino acid.

16. A method according to claim 15, wherein the amino acid is lysine or ornithine.

17. A method according to claim 14, wherein the amino functionalised solid material is obtained by reacting an acid or ester substituted support with a compound of formula (X)

$$H_2N-[(R^8)_zNH)]_y(R^{8'})_x-NH_2 \quad (X)$$

where x is an integer of 2 or more, y is 0 or an integer of 1 or more, and each group z is independently 2 or more, and each $R^8$ and $R^{8'}$ are the same or different and are optionally substituted divalent hydrocarbyl groups.

18. A method according to claim 17, wherein the compound of formula (X) is ethylenediamine.

19. A method according to claim 12, wherein the solid support comprises a solid support material comprising a compound of formula (IX)

[IX]

wherein S is a solid polymer core;
   $R^1$ is a organic moiety with n+1 available points for bonding:
   $R^2$ is an organic moiety with m+1 available points for bonding;
   $R^3$ is either a bond or an organic bridging group;
   L is a linkage agent, or a protected form thereof;
   p is an integer of 1 or more, provided that p is 1 when $R^3$ is a bond; and
   n and m are independently selected from integers of 2 or more.

20. A method according to claim 13, wherein the solid support comprises a solid support material comprising a compound of formula (IX)

[IX]

wherein S is a solid polymer core;
   $R^1$ is a organic moiety with n+1 available points for bonding:
   $R^2$ is an organic moiety with m+1 available points for bonding;
   $R^3$ is either a bond or an organic bridging group;
   L is a linkage agent, or a protected form thereof;
   p is an integer of 1 or more, provided that p is 1 when $R^3$ is a bond; and
   n and m are independently selected from integers of 2 or more.

21. A solid support obtained by the method of claim 2.
22. A solid support obtained by the method of claim 3.
23. A solid support obtained by the method of claim 4.
24. A solid support obtained by the method of claim 5.
25. A method according to claim 1, wherein step (iii) is carried out at least one time.

* * * * *